US012711322B2

United States Patent

(12) United States Patent
Sontag et al.

(10) Patent No.: US 12,711,322 B2
(45) Date of Patent: Aug. 18, 2026

(54) TECHNIQUES FOR REFINING QUERIES TO AN LLM-BASED SYSTEM FOR ANALYZING CLINICAL NOTES

(71) Applicant: LAYER HEALTH, INC., Brookline, MA (US)

(72) Inventors: David Alexander Sontag, Brookline, MA (US); Monica Nayan Agrawal, Boston, MA (US); Divya Gopinath, Millwood, NY (US); Steven Horng, Boston, MA (US); Luke Murray, Brooklyn, NY (US)

(73) Assignee: LAYER HEALTH, INC, Brookline, MA (US)

( * ) Notice: Subject to any disclaimer, the term of this patent is extended or adjusted under 35 U.S.C. 154(b) by 267 days.

(21) Appl. No.: 18/500,104

(22) Filed: Nov. 1, 2023

(65) Prior Publication Data

US 2025/0139384 A1 May 1, 2025

(51) Int. Cl.
*G16H 10/60* (2018.01)
*G06F 16/248* (2019.01)
*G06F 16/28* (2019.01)
*G06F 40/40* (2020.01)

(52) U.S. Cl.
CPC ............ *G06F 40/40* (2020.01); *G06F 16/248* (2019.01); *G06F 16/285* (2019.01); *G16H 10/60* (2018.01)

(58) Field of Classification Search
CPC ...... G06F 16/248; G06F 40/40; G06F 16/285; G16H 10/60
USPC ............................ 704/9, 202, 231–232, 251
See application file for complete search history.

(56) References Cited

U.S. PATENT DOCUMENTS

2025/0046409 A1* 2/2025 Thompson, IV ...... G16H 70/60

OTHER PUBLICATIONS

"Healthcare NLP: State of the Art Medical Language Models," accessed from <https://www.johnsnowlabs.com/healthcare-nlp/> on Jan. 17, 2024, John Snow LABS, Lewes, DE, USA.

Urban, et al., "What is Text Analytics for health?," Jul. 2023, <https://web.archive.org/web/20231101061930/ https://learn.microsoft.com/en-us/azure/ai-services/language-service/text-analytics-for-health/overview?tabs=ner>.

"Amazon Comprehend Medical," 2023, accessed from <https://aws.amazon.com/comprehend/medical/> on Jan. 17, 2024, Amazon Web Services, Inc.

(Continued)

*Primary Examiner* — George C Monikang
(74) *Attorney, Agent, or Firm* — Lando & Anastasi, LLP

(57) ABSTRACT

A method includes: (a) for each of a set of queries, receiving a specification of that query; (b) receiving an indication of a set of clinical notes; (c) for each query, prompting an LLM system based on the respective specification of that query and receiving a response from the LLM system to each query for each clinical note, each response including a label and evidence from that clinical note supporting the label; (d) for at least one query, displaying the label and evidence for each clinical note generated in response to the at least one query; (e) in response to displaying, receiving a revised specification of the at least one query; and (f) prompting the LLM system based on the revised specification of the at least one query and receiving an updated response from the LLM system to the at least one query for each clinical note, each updated response including an updated label and updated evidence from that clinical note supporting the updated label.

20 Claims, 8 Drawing Sheets

(56) References Cited

OTHER PUBLICATIONS

Bodenreider, “The Unified Medical Language System (UMLS): integrating biomedical terminology,” Nucleic Acids Research, 2004, pp. D267-D270, vol. 32 (Database issue).
“Healthcare Natural Language API,” Sep. 2023, <https://web.archive.org/web/20230926202744/https://cloud.google.com/healthcare-api/docs/concepts/nlp>.
“Embeddings,” accessed from <https://platform.openai.com/docs/guides/embeddings/what-are-embeddings> on Jan. 17, 2024, OpenAI.
Agrawal et al., “Large Language Models are Few-Shot Clinical Information Extractors”, arxiv.org, Cornell University Library, 201 Olin Library Cornell University Ithaca, NY 14853, Nov. 2022.
Alleva et al., “Keyword-optimized Template Insertion for Clinical Information Extraction via Prompt-based Learning”, arxiv.org, Cornell University Library, 201 Olin Library Cornell University Ithaca, NY 14853, Oct. 2023.
International Search Report and Written Opinion from corresponding International Application No. PCT/US2024/053590 dated Feb. 6, 2025.
Mishra et al., “PromptAid: Prompt Exploration, Perturbation, Testing and Iteration using Visual Analytics for Large Language Models”, arxiv.org, Cornell University Library, 201 Olin Library Cornell University Ithaca, NY 14853, Apr. 2023.
Yang et al., “Towards Interpretable Mental Health Analysis with Large Language Models”, arxiv.org, Cornell University Library, 201 Olin Library Cornell University Ithaca, NY 14853, Oct. 2023.

* cited by examiner

Fig. 2A
100
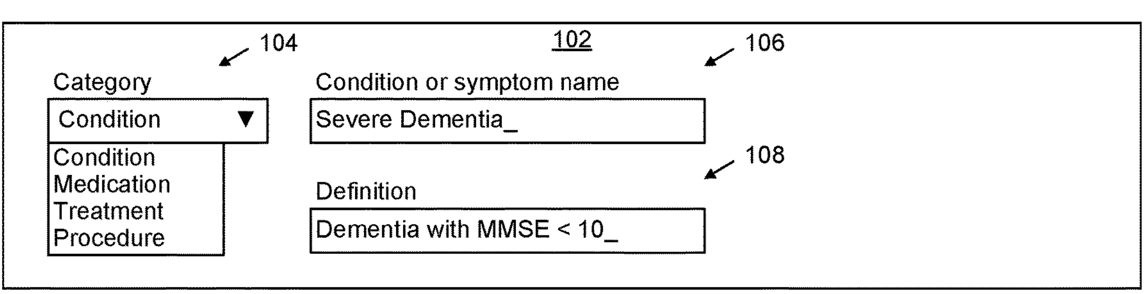
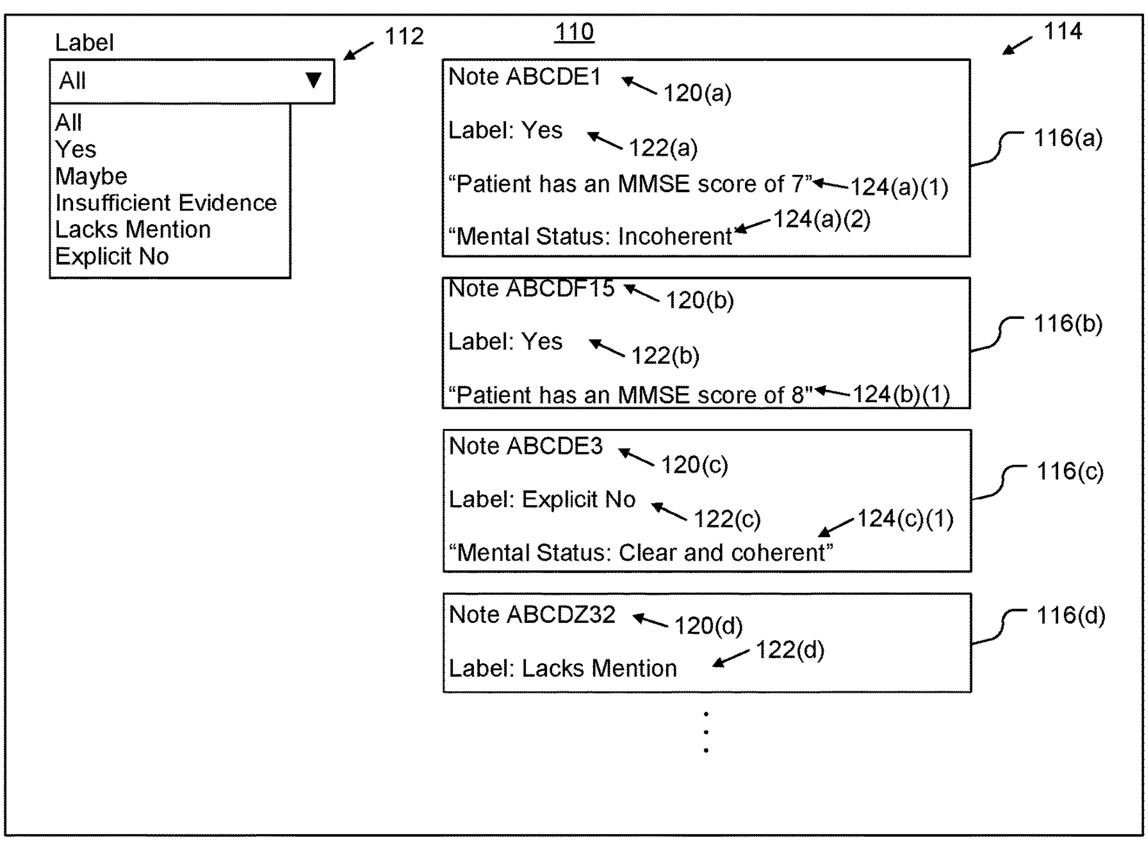

Fig. 2B
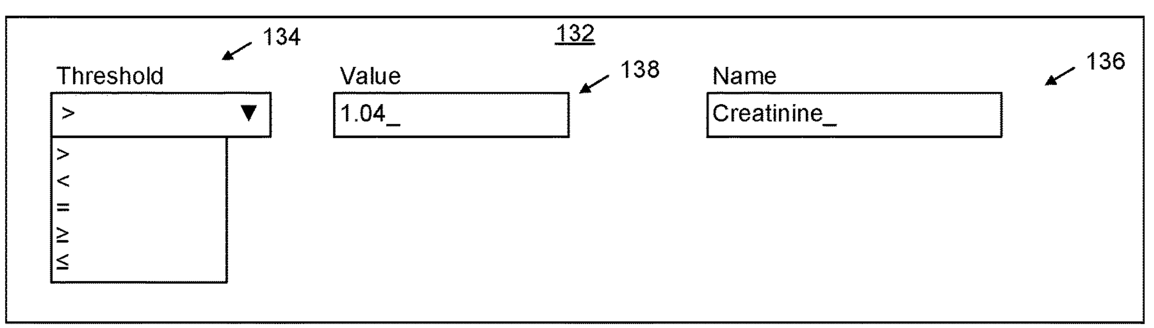
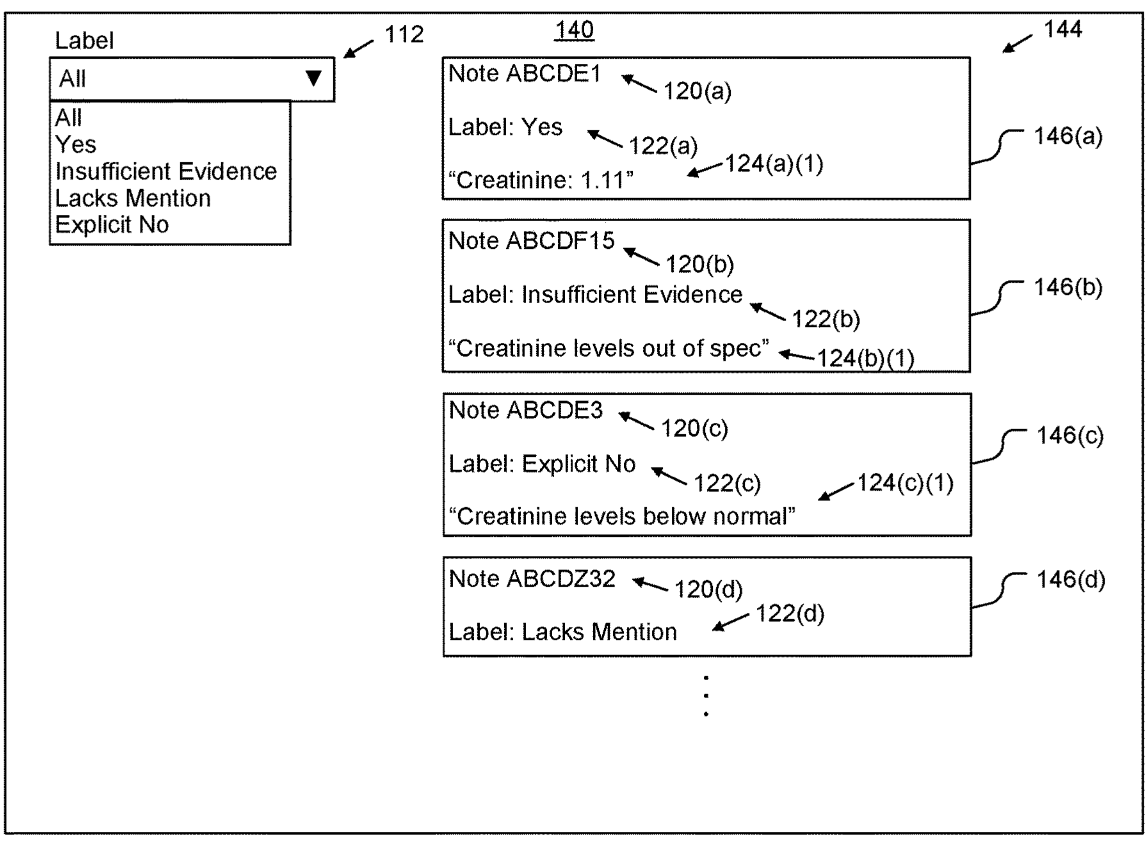

Fig. 2C
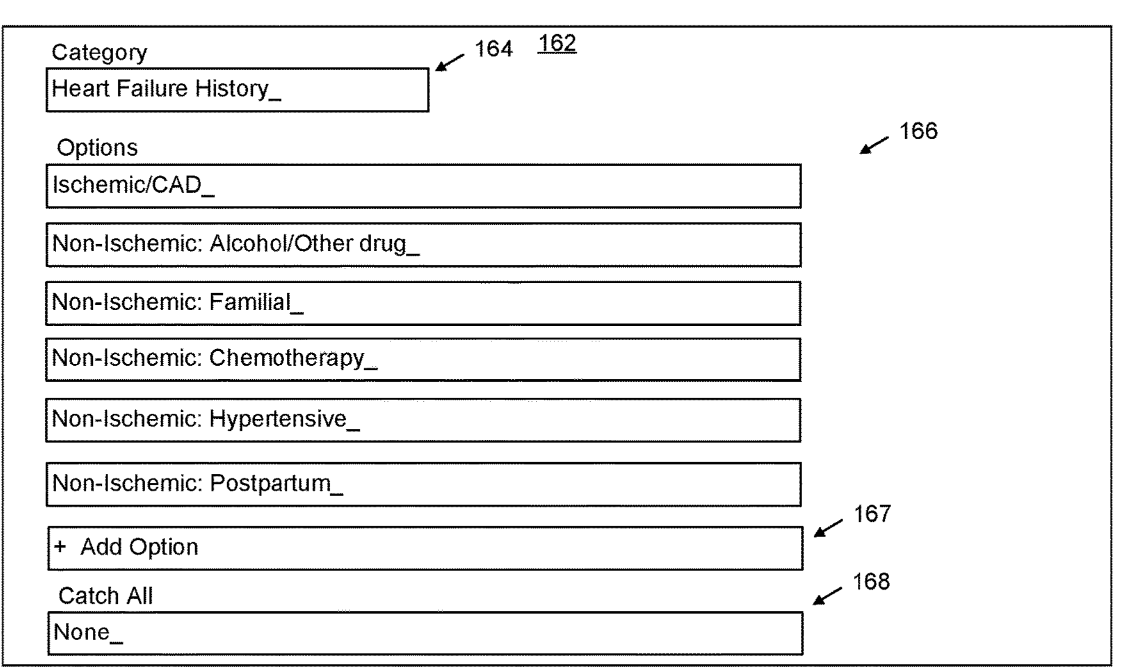
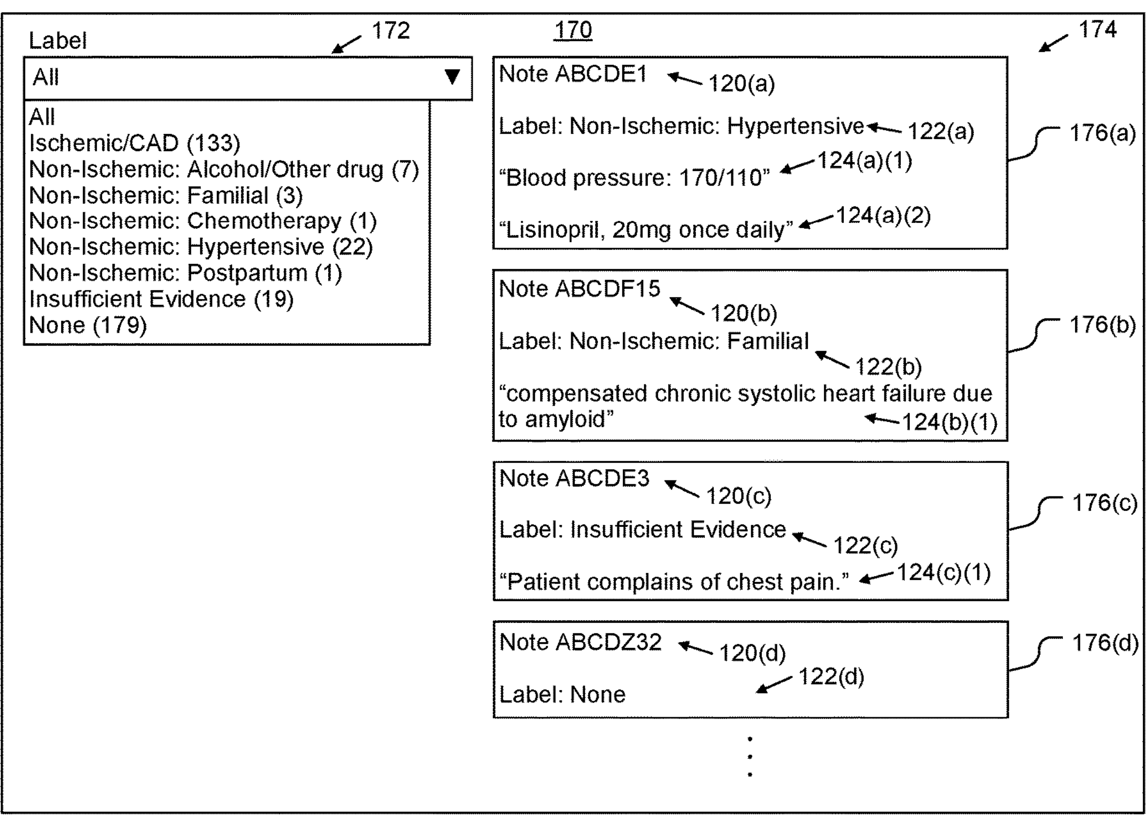

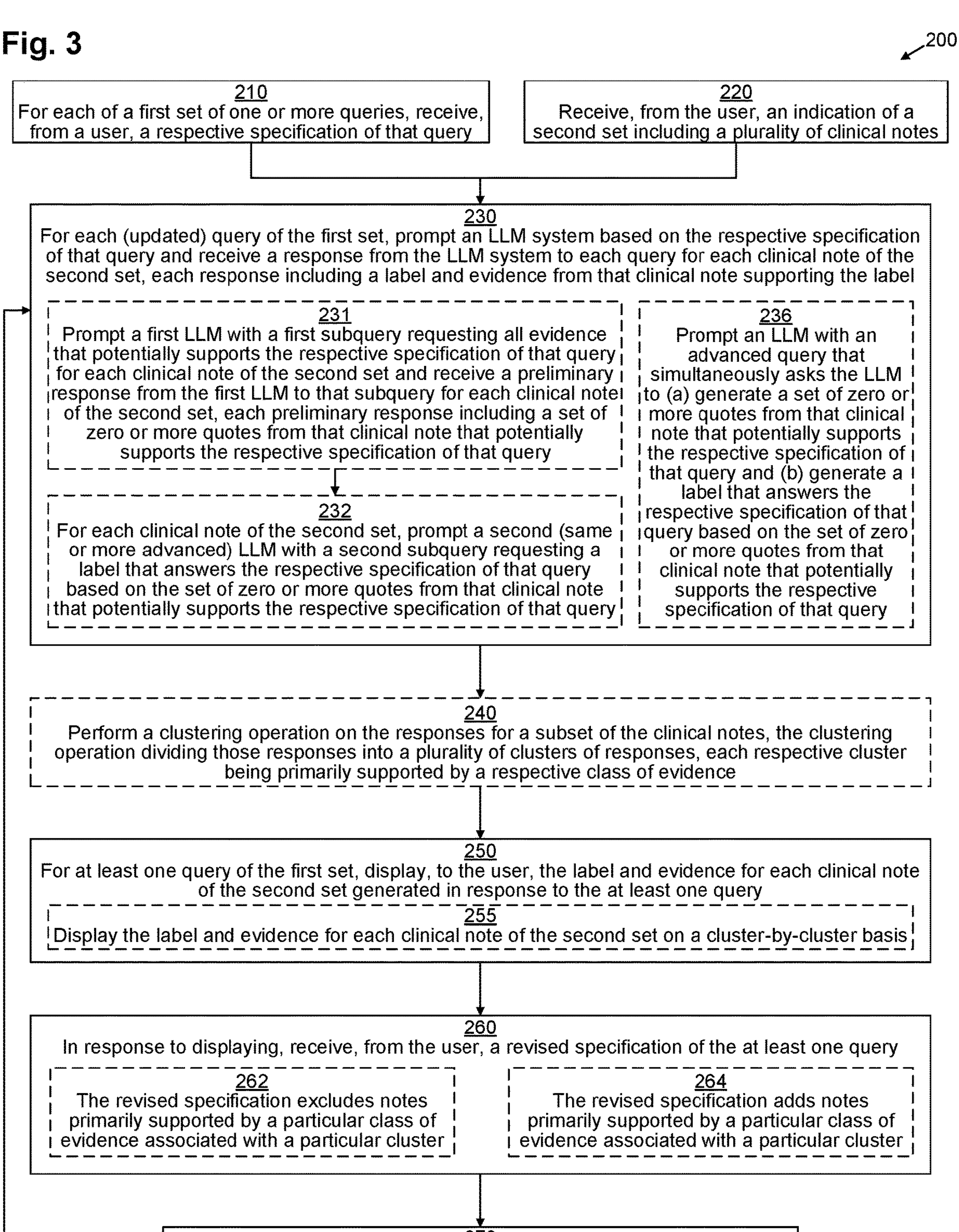
Fig. 3
200
210
For each of a first set of one or more queries, receive, from a user, a respective specification of that query
220
Receive, from the user, an indication of a second set including a plurality of clinical notes
230
For each (updated) query of the first set, prompt an LLM system based on the respective specification of that query and receive a response from the LLM system to each query for each clinical note of the second set, each response including a label and evidence from that clinical note supporting the label
231
Prompt a first LLM with a first subquery requesting all evidence that potentially supports the respective specification of that query for each clinical note of the second set and receive a preliminary response from the first LLM to that subquery for each clinical note of the second set, each preliminary response including a set of zero or more quotes from that clinical note that potentially supports the respective specification of that query
232
For each clinical note of the second set, prompt a second (same or more advanced) LLM with a second subquery requesting a label that answers the respective specification of that query based on the set of zero or more quotes from that clinical note that potentially supports the respective specification of that query
236
Prompt an LLM with an advanced query that simultaneously asks the LLM to (a) generate a set of zero or more quotes from that clinical note that potentially supports the respective specification of that query and (b) generate a label that answers the respective specification of that query based on the set of zero or more quotes from that clinical note that potentially supports the respective specification of that query
240
Perform a clustering operation on the responses for a subset of the clinical notes, the clustering operation dividing those responses into a plurality of clusters of responses, each respective cluster being primarily supported by a respective class of evidence
250
For at least one query of the first set, display, to the user, the label and evidence for each clinical note of the second set generated in response to the at least one query
255
Display the label and evidence for each clinical note of the second set on a cluster-by-cluster basis
260
In response to displaying, receive, from the user, a revised specification of the at least one query
262
The revised specification excludes notes primarily supported by a particular class of evidence associated with a particular cluster
264
The revised specification adds notes primarily supported by a particular class of evidence associated with a particular cluster
270
Update the at least one query with the revised specification

Fig. 4

TECHNIQUES FOR REFINING QUERIES TO AN LLM-BASED SYSTEM FOR ANALYZING CLINICAL NOTES

BACKGROUND

Medical providers take detailed clinical notes about their interactions with patients. There is a wealth of health information embedded within these clinical notes. In order to extract this information in a useful way, trained health professionals may read through the clinical notes (sometimes referred to as "chart review") and enter data into structured forms or databases, allowing the medical information to be analyzed in bulk.

Another way to extract useful information from clinical notes involves performing keyword searches, and having trained health professionals review the search results to reduce the amount of reading required.

SUMMARY

The above conventional techniques for extracting useful information from clinical notes have drawbacks. Having trained health professionals read through all the clinical notes is tedious, time-consuming, and prone to user error. Performing a preliminary search may reduce the time to an extent, but it is still time-consuming, and it also adds an additional possibility of missing information that is not flagged by search. Developing machine learning models for each specific information element is also time-consuming, as it requires first having health professionals review a large number of clinical notes to label data to obtain the ground-truth needed for machine learning.

Thus, it would be desirable for a system to be able to automatically analyze and extract useful information from a large set of clinical notes without needing a person to explicitly label them. This may be accomplished by using a large language model (LLM)-based system to perform a set of queries on the large set of clinical notes. However, generating the appropriate queries can be a challenge. In order to generate the set of queries, a user may enter natural language queries using a specialized interface and run those queries through the LLM-based system. The specialized interface for entering the queries allows the user to test the queries against a test set of clinical notes (possibly including real clinical notes from real doctors examining real patients). In response, the system displays query responses for each note together with evidence supporting those responses drawn from the clinical notes. In some embodiments, a clustering operation is performed so that the user can better understand different categories of response. The user is then able to go back and alter one or more of the queries until the desired results are achieved. Subsequently, the set of queries can then be run through the LLM system on actual clinical notes to achieve the desired results, such as, for example, filling out a set of structured forms or a database. In some embodiments, the LLM system includes breaking each query up into a first and second subquery, each of which may be fed separately into the same or different LLMs. In other embodiments, a single LLM may process each query in an atomic operation.

In one embodiment, a method is performed by a computing system. The method includes: (a) for each of a first set of one or more queries, receiving, from a user, a respective specification of that query; (b) receiving, from the user, an indication of a second set including a plurality of clinical notes; (c) for each query of the first set, prompting a large language model (LLM) system based on the respective specification of that query and receiving a response from the LLM system to each query for each clinical note of the second set, each response including a label and evidence from that clinical note supporting the label; (d) for at least one query of the first set, displaying, to the user, the label and evidence for each clinical note of the second set generated in response to the at least one query; (e) in response to displaying, receiving, from the user, a revised specification of the at least one query; and (f) prompting the LLM system based on the revised specification of the at least one query and receiving an updated response from the LLM system to the at least one query for each clinical note of the second set, each updated response including an updated label and updated evidence from that clinical note supporting the updated label. Corresponding apparatuses, systems, and computer program products for performing the method are also provided.

BRIEF DESCRIPTION OF THE DRAWINGS

The foregoing and other objects, features, and advantages will be apparent from the following description of particular embodiments, as illustrated in the accompanying drawings in which like reference characters refer to the same parts throughout the different views. The drawings are not necessarily to scale, emphasis instead being placed upon illustrating the principles of various embodiments.

FIGS. 2A-C illustrate example query input and feedback interfaces in accordance with one or more embodiments.

FIG. 3 illustrates an example method in accordance with one or more embodiments.

FIG. 4 illustrates an example clustering interface in accordance with one or more embodiments.

DETAILED DESCRIPTION

Figure 1:
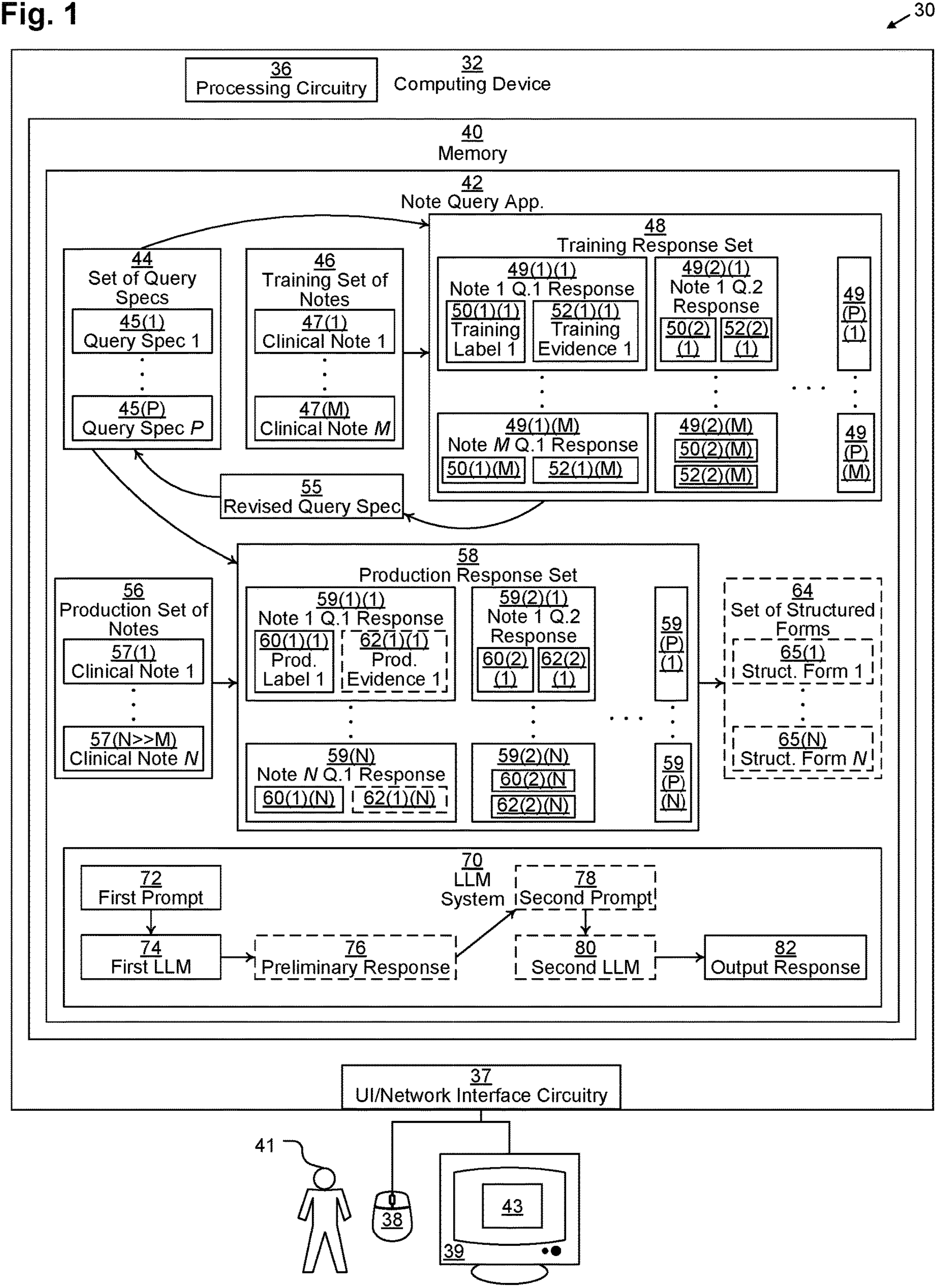
FIG. 1 illustrates an example system, apparatus, computer program product, and associated data structures for use in connection with one or more embodiments.

FIG. 1 depicts an example system 30 for use in connection with various embodiments.

System 30 includes a computing device 32, one or more input devices 38, one or more display devices 39, and a user 41.

Computing device 32 may be any kind of computing device, such as, for example, a personal computer, laptop, workstation, server, enterprise server, tablet, smartphone, etc. Computing device 32 may include processing circuitry 36, interface circuitry 37 (e.g., user interface (UI) and/or network interface circuitry), and memory 40. Computing device 32 may also include various additional features as is well-known in the art, such as, for example, interconnection buses, etc.

Processing circuitry 36 may include any kind of processor or set of processors configured to perform operations, such as, for example, a microprocessor, a multi-core microprocessor, a digital signal processor, a system on a chip (SoC), a collection of electronic circuits, a similar kind of controller, or any combination of the above.

As depicted in FIG. 1, user 41 directly interfaces with computing device 32 using the one or more input devices 38 and the one or more display devices 39, which are connected via the interface circuitry 37 (e.g., UI circuitry). UI circuitry may include any circuitry needed to communicate with and connect to the one or more input devices 38 and display devices 39. The UI circuitry may include, for example, a keyboard controller, a mouse controller, a touch controller, a serial bus port and controller, a universal serial bus (USB) port and controller, a wireless controller and antenna (e.g., Bluetooth), a graphics adapter and port, etc.

A display device 39 may be any kind of display, including, for example, a CRT screen, LCD screen, LED screen, etc. Input device(s) 38 may include a keyboard, keypad, mouse, trackpad, trackball, pointing stick, joystick, touchscreen (e.g., embedded within display device 39), microphone/voice controller, etc. In some embodiments, instead of being external to computing device 32, the input device 38 and/or display device 39 may be embedded within the computing device 32 (e.g., a cell phone or tablet with an embedded touchscreen). Display device 39 displays a UI 43 to the user 41, and user 41 can enter information into the UI 43 using the one or more input devices 38.

In other embodiments (not depicted), user 41 uses the one or more input devices 38 and display devices 39 to interface with remote UI circuitry (not depicted) on a remote computing device (not depicted) that communicates with the computing device 32 across a network (not depicted). In such a case, the interface circuitry 37 of the computing device 32 may be network interface circuitry, which may include one or more Ethernet cards, cellular modems, Fibre Channel (FC) adapters, InfiniBand adapters, wireless networking adapters (e.g., Wi-Fi), and/or other devices for connecting to a network. The network may be any kind of communications network or set of communications networks, such as, for example, a LAN, WAN, SAN, the Internet, a wireless communication network, a virtual network, a fabric of interconnected switches, etc.

Memory 40 may include any kind of digital system memory, such as, for example, random access memory (RAM). Memory 40 stores an operating system (OS, not depicted, e.g., a Linux, UNIX, Windows, MacOS, or similar operating system), a note query application 42, and various drivers and other applications and software modules configured to execute on processing circuitry 36 as well as various data.

In operation, note query application 42 receives a set 44 of query specifications 45 (depicted as query specifications 45(1), . . . , 45(P)) and a training set 46 of clinical notes 47 (depicted as clinical notes 47(1), . . . , 47(M)) and generates a training response set 48 having responses 49 to the P queries specified by the query specifications 45 for each of the M clinical notes 47 by querying large language model (LLM) system 70 with the set 44 of query specifications 45 for the training set 46 of clinical notes 47. Thus, there are P×N responses 49 (depicted as response 49(1)(1) to query 1 for note 1, response 49(1)(M) to query 1 for note M, response 49(2)(1) to query 2 for note 1, response 49(2)(M) to query 2 for note M, response 49(P)(1) to query P for note 1, and response 49(P)(M) to query P for note M) in training response set 48. Each response 49 includes a respective training label 50 and training evidence 52 (i.e., response 49(X)(Y) includes training label 50(X)(Y) and training evidence 52(X)(Y)). A training label 50(X)(Y) represents an "answer" to the Xth query based on note Y (e.g., "Yes"). Training evidence 52(X)(Y) may include zero or more quotations from note Y that supports the answer of training label 50(X)(Y). Note query application 42 displays details from the training response set 48 within a user interface (UI) 43 displayed on the display screen 39. Clinical notes 47 may include any kind of electronic records having a plaintext representation, such as, for example, electronic medical records, text files, PDF versions of medical records, images of scanned documents which have been processed using optical character recognition, etc.

When the user 41 enters a revised query specification 55 for a particular query (e.g., revised query specification 55 represents an updated version of the Pth query), note query application 42 updates the set 44 of query specifications 45 with the revised query specification 55 (so revised query specification 55 replaces query specification 45(P) within set 44). Once the user 41 has finished entering revised query specifications 55, note query application 42 resubmits the (now updated) set 44 of query specifications 45 for the training set 46 of clinical notes 47 to the LLM system 70 to update the training response set 48.

Once the user 41 is satisfied with the training response set 48, the set 44 of query specifications 45 is finalized, allowing the user 41 (who may or may not be the same user who input and validated the set 44 or query specifications 45) to generate a production response set 58 of production responses 59 based on a production set 56 of N clinical notes 57 (depicted as clinical notes 57(1), . . . , 57(N)) for N much larger than M using the LLM system 70 with reference to the finalized set 44 of query specifications 45. Thus, there are P×N responses 59 (depicted as response 59(1)(1) to query 1 for note 1, response 59(1)(N) to query 1 for note N, response 59(2)(1) to query 2 for note 1, response 59(2)(N) to query 2 for note N, response 59(P)(1) to query P for note 1, and response 59(P)(N) to query P for note N) in production response set 58. Each response 59 includes a respective production label 60. In some embodiments, each response 59 may also include production evidence 62 (i.e., note 59(X)(Y) includes production label 60(X)(Y) and, in some embodiments, production evidence 62(X)(Y)). A production label 60(X)(Y) represents an "answer" to the Xth query based on note Y (e.g., "Maybe"). Production evidence 62(X)(Y) may include zero or more quotations from note Y that supports the answer of production label 60(X)(Y). In some embodiments, note query application 42 may also operate to generate a set 64 of structured forms 65 (depicted as structured forms 65(1), . . . , 65(N)). Note query application 42 displays details from the production response set 58 and/or the set 64 of structured forms 65 within the UI 43 displayed on the display screen 39.

LLM system 70 includes at least a first LLM 74, which is fed a first prompt 72 for a particular query (based on a query specification 45). LLM system 70 outputs an output response 82 to that first prompt 72. Output response 82 may be used as a label 50, 60. In some embodiments, the first prompt 72 is equivalent to the query specification 45 (possibly with additional words added), and the output response 82 is generated as the output of the first LLM 74 in response to the first query 72.

In other embodiments, the first prompt 72 represents a subquery generated from the query specification 45. For example, if the query specification 45 defines a query requesting whether or not a patient has heart disease based on a clinical note 47, 57, the first prompt may ask "Does the input clinical note provide evidence that the patient has heart disease? Return all snippets from the input clinical note that support or deny this conclusion." All snippets or quotations from the clinical note 47, 57 that support a conclusion of heart disease in the patient would be returned in a preliminary response 76. Then, LLM system 70 generates a second prompt 78, based on the preliminary response 76, to feed into second LLM 80. In some embodiments, second LLM 80 is identical to the first LLM 74, but there are multiple calls to the same LLM performed for the same query, while in other embodiments, two different LLMs 74, 80 are used. Continuing in the previous example, the second prompt might be "Do the snippets, when analyzed together, imply or strongly suggest that the patient has heart disease? Answer (A) Patient has heart disease, (B) Evidence suggests possible heart disease, (C) Evidence against heart disease, (D) Inconclusive evidence, or (E) No evidence or insufficient evidence. Include quotes to justify the answer." The output of the second LLM 80 is the output response 82.

LLMs 74, 80 may be any kind of LLM trained on a large set of training data. In some embodiments, second LLM 80 may be more advanced than first LLM 74 (e.g., it may be able to receive larger sets of input text and/or it may be trained on a larger set of data). For example, first LLM 74 may be GPT 3.5 or GPT 3.5 Turbo provided by OpenAI, Inc. of San Francisco, CA, while second LLM 74 may be GPT 4 also provided by OpenAI, Inc.

Memory 40 may also store various other data structures used by the OS, note query application 42, LLM system 70, and/or various other applications and drivers. In some embodiments, memory 40 may also include a persistent storage portion. Persistent storage portion of memory 40 may be made up of one or more persistent storage devices, such as, for example, magnetic disks, flash drives, solid-state storage drives, or other types of storage drives. Persistent storage portion of memory 40 is configured to store programs and data even while the computing device 32 is powered off. The OS, note query application 42, LLM system 70, and/or various other applications and drivers are typically stored in this persistent storage portion of memory 40 so that they may be loaded into a system portion of memory 40 upon a system restart or as needed. The OS, note query application 42, LLM system 70, and/or various other applications and drivers, when stored in non-transitory form either in the volatile or persistent portion of memory 40 (which may be referred to as a non-transitory computer-readable storage medium), each form a computer program product. The processing circuitry 36 running one or more applications thus forms a specialized circuit constructed and arranged to carry out the various processes described herein.

In some embodiments (not depicted), instead of the above-described functions of computing device 32 being performed entirely by processing circuitry 36 of a single computing device 32 with corresponding data stored entirely within memory 40 of computing device 32, the functions and data may be distributed across several computing devices communicatively coupled via a network.

FIGS. 2A-2C depict different configurations of the UI 43 for entering and validating the query specifications 45.

FIG. 2A depicts a binary query configuration 100 of the UI 43 used for entering and validating a query specification 45 representing a binary query. A binary query asks a question which, in theory, should have a yes or no answer. However, although referred to as a "binary" query, it need not be strictly binary, since there may not always be enough information to make a definitive decision.

Binary query input window 102 includes a dropdown box 104 that allows a user 41 to select from a variety of categories, a condition/symptom name text box 106, and a definition text box 108. As depicted, the category options are "condition," "medication," "treatment," and "procedure," and the "condition" category is selected. In some embodiments, additional category options may also be available, such as, for example, a "status" option to describe a performance status, a cancer mutation status, a hormone receptor status, etc. As depicted in FIG. 2A, the user 41 has entered "Severe Dementia" into the condition/symptom name text box 106, and the user 41 has also entered "Dementia with MMSE<10" into the definition text box 108. The selection of a binary query type as well as the values entered in boxes 104, 106, 108 define a particular query specification 45. In this case, the query specification 45 represents a query asking whether or not a clinical note 47, 57 indicates that the patient has a medical condition of severe dementia, which is further defined as having an MMSE score below 10. The values entered into text boxes 106, 108 may be natural language descriptions, since they will be interpreted by an LLM 74, 80.

Binary query validation window 110 includes a dropdown box 112 that allows a user 41 to select from a variety of labels 122 and a set 114 of binary query responses 116 (depicted as binary query responses 116(*a*), 116(*b*), 116(*c*), 116(*d*), . . . ) for the various clinical notes 47 of the training set 46. As depicted, the possible labels 122 for a binary query response 116 are "yes," "maybe," "insufficient evidence," "lacks mention," and "explicit no." As depicted, dropdown box 112 shows a selection of "all," meaning that binary query responses 116 having any label 122 are shown in set 114. Each binary query response 116 includes a note identifier 120 and a label 122. Some binary query responses 116 may also include one or more pieces of evidence 124 (e.g., snippets or quotes from the clinical note 47 identified by the note identifier 120). As depicted, binary query response 116(*a*) has note identifier 120(*a*), identifying the binary query response 116(*a*) as representing clinical note ABCDE1; binary query response 116(*b*) has note identifier 120(*b*), identifying the binary query response 116(*b*) as representing clinical note ABCDF15; binary query response 116(*c*) has note identifier 120(*c*), identifying the binary query response 116(*c*) as representing clinical note ABCDE3; and binary query response 116(*d*) has note identifier 120(*d*), identifying the binary query response 116(*d*) as representing clinical note ABCDZ32.

As depicted, binary query response 116(*a*) has label 122(*a*), indicating that the training label 50 assigned in response to the binary query for clinical note ABCDE1 is "yes," meaning that the patient has been positively identified as having severe dementia. This evaluation is supported by two pieces of evidence: 124(*a*)(1) "Patient has an MMSE score of 7" and 124(*a*)(2) "Mental Status: Incoherent."

As depicted, binary query response 116(*b*) has label 122(*b*), indicating that the training label 50 assigned in response to the binary query for clinical note ABCDF15 is "yes," meaning that the patient has been positively identified as having severe dementia. This evaluation is supported by one piece of evidence: 124(*b*)(1) "Patient has an MMSE score of 8."

As depicted, binary query response 116(*c*) has label 122(*c*), indicating that the training label 50 assigned in response to the binary query for clinical note ABCDE3 is "explicit no," meaning that the patient has been positively identified as NOT having severe dementia. This evaluation is supported by one piece of evidence: 124(*c*)(1) "Mental Status: Clear and coherent."

As depicted, binary query response 116(*d*) has label 122(*d*), indicating that the training label 50 assigned in response to the binary query for clinical note ABCDZ32 is "lacks mention," meaning that the clinical note 47 does not indicate one way or the other whether the patient has severe dementia. This evaluation is supported by the lack of any pieces of evidence 124 from the clinical note 47.

Although not depicted, a label 122 of "Maybe" would indicate that there is some evidence for severe dementia in the clinical note 47, but it is not strong enough to be sure. Although not depicted, a label 122 of "Insufficient Evidence" would indicate that there is evidence both in support of severe dementia and against severe dementia in the clinical note 47.

Were the user 41 to select a different label 122 in dropdown box 112, then the set 114 would be filtered to only include binary query responses 116 having that label 122. Thus, if the user 41 were to select "yes," then binary query responses 116(*a*), 116(*b*) would remain, but binary query responses 116(*c*), 116(*d*) would be replaced by other binary query responses 116 having labels 122 of "yes."

FIG. 2B depicts a threshold query configuration 130 of the UI 43 used for entering and validating a query specification 45 representing a threshold query. A threshold query asks a question about whether a particular numerical value meets a particular threshold condition. Similar to a binary query, since there may not always be enough information to make a definitive decision, the label 11 in response may take values other than "yes" or "explicit no."

Threshold query input window 132 includes a dropdown box 134 that allows a user 41 to select from a variety of threshold comparators, a value text box 138, and a name text box 136. As depicted, the threshold comparator options are ">," "<," "," ">" and "," and the ">" threshold comparator is selected. The user 41 has entered a value of 1.04 into the value text box 138, and the user 41 has also entered "Creatinine" into the name text box 136. The selection of a threshold query type as well as the values entered in boxes 134, 136, 138 define a particular query specification 45. In this case, the query specification 45 represents a query asking whether or not a clinical note 47, 57 indicates that the patient has a creatinine level greater than 1.04.

Threshold query validation window 140 includes a dropdown box 112 that allows a user 41 to select from a variety of labels 122 and a set 144 of threshold query responses 146 (depicted as threshold query responses 146(*a*), 146(*b*), 146(*c*), 146(*d*), . . . ) for the various clinical notes 47 of the training set 46. As depicted, the possible labels 122 for a threshold query response 146 are "yes," "insufficient evidence," "lacks mention," and "explicit no." As depicted, dropdown box 112 shows a selection of "all," meaning that threshold query responses 146 having any label 122 are shown in set 114. Each threshold query response 146 includes a note identifier 120 and a label 122. Some threshold query responses 146 may also include one or more pieces of evidence 124.

As depicted, threshold query response 146(*a*) has label 122(*a*), indicating that the training label 50 assigned in response to the threshold query for clinical note ABCDE1 is "yes," meaning that the patient has been positively identified as having a creatinine level above the threshold value. This evaluation is supported by one piece of evidence: 124(*a*)(1) "Creatinine: 1.11."

As depicted, threshold query response 146(*b*) has label 122(*b*), indicating that the training label 50 assigned in response to the threshold query for clinical note ABCDF15 is "insufficient evidence," meaning that it is unclear whether the patient has a creatinine level above the threshold value. This evaluation is supported by one piece of evidence: 124(*b*)(1) "Creatinine levels out of spec." It is not clear whether the creatinine levels are very high or very low.

As depicted, threshold query response 146(*c*) has label 122(*c*), indicating that the training label 50 assigned in response to the threshold query for clinical note ABCDE3 is "explicit no," meaning that the patient has been positively identified as NOT having a creatinine level above the threshold value. This evaluation is supported by one piece of evidence: 124(*c*)(1) "Creatinine levels below normal." It should be noted that even though the creatinine level is not explicitly mentioned in the chart, the LLM 74, 80 is able to understand that a level below normal is below 1.04.

As depicted, threshold query response 146(*d*) has label 122(*d*), indicating that the training label 50 assigned in response to the threshold query for clinical note ABCDZ32 is "lacks mention," meaning that the clinical note 47 does not indicate one way or the other whether the patient has a creatinine level above the threshold value. This evaluation is supported by the lack of any pieces of evidence 124 from the clinical note 47.

Although not depicted, a label 122 of "Insufficient Evidence" would indicate that there is evidence both in support of a creatinine level above 1.04 and against a creatinine level above 1.04 in the clinical note 47.

Were the user 41 to select a different label 122 in dropdown box 112, then the set 114 would be filtered to only include threshold query responses 146 having that label 122. Thus, if the user 41 were to select "insufficient evidence," then threshold query response 146(*b*) would remain, but threshold query responses 146(*a*), 146(*c*), 146(*d*) would be replaced by other threshold query responses 146 having labels 122 of "insufficient evidence."

FIG. 2C depicts a multiple-choice query configuration 160 of the UI 43 used for entering and validating a query specification 45 representing a multiple-choice query. A multiple-choice query asks which of a variety of values a particular category fits into.

Multiple-choice query input window 162 includes a category text box 164 that allows a user 41 to enter a category, a set of option text boxes 166, an add option button 167, and a catch all text box 168. As depicted, the category is "heart failure history," and the options entered into the set of option text boxes 166 are "ischemic/CAD," "non-ischemic: alcohol or other drug," "non-ischemic: familial," "non-ischemic: chemotherapy," "non-ischemic: hypertensive," and "non-ischemic: postpartum," indicating several common etiologies for heart failure history. If the user 41 wants to add another etiology, the user 41 may select the add option button 167 to create another option text box 166. Catch all text box 168 allows the user to provide a name for a catch all option that doesn't satisfy any of the other options (aside from "insufficient evidence"), which, as depicted, is "none." The selection of a multiple-choice query type as well as the values entered in boxes 164, 166, 168 define a particular query specification 45. In this case, the query specification 45 represents a query asking what the etiology of the patient's heart failure history is, with a list of specific options to be selected from. The values entered into text boxes 166, 168 may be natural language descriptions, since they will be interpreted by an LLM 74, 80. In some embodiments (not depicted), a definition text box 108 may be used in connection with one or more of the option text boxes 166 to allow the user 41 to provide a more precise definition of the terms in those option text boxes 166.

Multiple-choice query validation window 170 includes a dropdown box 172 that allows a user 41 to select from a variety of labels 122 and a set 174 of multiple-choice query responses 176 (depicted as multiple-choice query responses 176(*a*), 176(*b*), 176(*c*), 176(*d*), . . . ) for the various clinical notes 47 of the training set 46. As depicted, the possible labels 122 for a multiple-choice query response 146 are the values that the user 41 listed in the set of option text boxes 166, 168 plus "insufficient evidence." As depicted, dropdown box 112 shows a selection of "all," meaning that multiple-choice query responses 176 having any label 122 are shown in set 174. Each multiple-choice query response 176 includes a note identifier 120 and a label 122. Some multiple-choice query responses 176 may also include one or more pieces of evidence 124.

As depicted, multiple-choice query response 176(*a*) has label 122(*a*), indicating that the training label 50 assigned in response to the multiple-choice query for clinical note ABCDE1 is "non-ischemic: hypertensive," meaning that the etiology of the patient's heart failure history has been positively identified as being non-ischemic and being due to hypertension. This evaluation is supported by two pieces of evidence: 124(*a*)(1) "Blood pressure 170/110" and 124(*a*)(2) "Lisinopril, 20 mg once daily."

As depicted, multiple-choice query response 176(*b*) has label 122(*b*), indicating that the training label 50 assigned in response to the multiple-choice query for clinical note ABCDF15 is "non-ischemic: familial," meaning that that the etiology of the patient's heart failure history has been positively identified as being non-ischemic and being due to an inherited condition. This evaluation is supported by one piece of evidence: 124(*b*)(1) "compensated chronic systolic heart failure due to amyloid."

As depicted, multiple-choice query response 176(*c*) has label 122(*c*), indicating that the training label 50 assigned in response to the multiple-choice query for clinical note ABCDE3 is "insufficient evidence," meaning that there is insufficient evidence to identify the etiology of the patient's heart failure. This evaluation is supported by one piece of evidence: 124(*c*)(1) "Patient complains of chest pain," indicating that there is likely a heart condition, but the etiology is not certain.

As depicted, multiple-choice query response 176(*d*) has label 122(*d*), indicating that the training label 50 assigned in response to the multiple-choice query for clinical note ABCDZ32 is "none," meaning that the clinical note 47 does not indicate one way or the other whether the patient even has any heart failure history. This evaluation is supported by the lack of any pieces of evidence 124 from the clinical note 47.

Were the user 41 to select a different label 122 in dropdown box 112, then the set 114 would be filtered to only include multiple-choice query responses 176 having that label 122. Thus, if the user 41 were to select "non-ischemic: familial," then multiple-choice query response 176(*b*) would remain, but multiple-choice query responses 176(*a*), 176(*c*), 176(*d*) would be replaced by other multiple-choice query responses 176 having labels 122 of "non-ischemic: familial."

It should be understood that although FIGS. 2A-2C depict query configurations 100, 130, 160 of the UI 43, other query configurations for other types of queries may also be possible.

FIG. 3 illustrates an example method 200 performed by a system 30 for configuring a set 44 of query specifications 45. It should be understood that any time a piece of software (e.g., OS, note query application 42, LLM system 70, first LLM 74, second LLM 80, etc.) is described as performing a method, process, step, or function, what is meant is that a computing device 32 on which that piece of software is running performs the method, process, step, or function when executing that piece of software on its processing circuitry 36. It should be understood that one or more of the steps or sub-steps of method 200 may be omitted in some embodiments. Similarly, in some embodiments, one or more steps or sub-steps may be combined together or performed in a different order.

In step 210, note query application 42 receives from user 41, for each of a first set of one or more queries, a respective specification 45 of that query. In some embodiments, step 210 may include displaying a binary query input window 102, a threshold query input window 132, or a multiple-choice query input window 162 in UI 43 for each query of the first set of queries to allow the user 41 to input a binary query specification, a threshold query specification, or a multiple-choice query specification as described above in connection with FIGS. 2A, 2B, and 2C. In some embodiments, entering the query specification may include entering a detailed definition into a definition text box 108, such as in the case of a binary query specification or a multiple-choice query specification. In some embodiments (not depicted), user 41 may also input a query specification by uploading a dictionary definition file (not depicted) that defines a term used in the query specification in detail. The definition file, if provided, defines the specific criteria for when the system should return a label, such as the rise of a specific biomarker, specific pathologic or imaging evidence, or specific symptoms of a condition. In some embodiments (not depicted), aspects of the query definition may be programmatically defined via an API. Upon completion of step 210, the set 44 of P query specifications 45 will have been received and stored in memory 40.

In step 220, which may be performed in parallel with step 210 (e.g., step 220 may be performed either before or after step 210), note query application 42 receives from user 41, an indication of a training set 46 of clinical notes 47. Step 220 may include user 41 selecting a location where the training set 46 is stored, the user 41 scanning in or copying the training set 46 into memory 40, the user 41 typing in the clinical notes 47 of training set 46, or some combination of these (e.g., some clinical notes 47 are scanned, some are uploaded, and some are typed in by the user 41).

In step 230, for each query of the first set, note query application 42 prompts LLM system 70 based on the respective specification 45 of that query (with first prompt 72) and receives a response 49, 82 from the LLM system 70 to each query for each clinical note 47 of the training set 46, each response 49, 82 including a label 50 and evidence 52 from that clinical note 47 supporting the label 50. Thus, for all M training notes 47, there are P responses 49 (1-P) (1-M), and training response set 48 has P×M responses 49.

In some embodiments, step 230 may include sub-steps 231, 232 for each query of the first set, while in other embodiments, step 230 includes sub-step 236 for each query of the first set.

In sub-step 231, LLM system 70 prompts first LLM 74 with a first subquery (e.g., first prompt 72) requesting all evidence that potentially supports the specification 45 of a query for each clinical note 47 of the training set 46, yielding a preliminary response 76 from the first LLM 74 to that subquery for each clinical note 47 of the training set 46. Each preliminary response 76 includes a set of zero or more quotes from its corresponding clinical note 47 that potentially supports the specification 45 of the query. For example, with reference to FIG. 2A, the first prompt 72 may ask "Does the input clinical note provide evidence that the patient has severe dementia with an MMSE less than 10? Return all snippets from the input clinical note that support or deny this conclusion." In response, for clinical note ABCDE1, the preliminary response 76 may include several quotes, including "Patient has an MMSE score of 7," "Mental Status: Incoherent," and "Patient was evaluated for dementia."

In sub-step 232, for each clinical note 47 of the training set 46, LLM system 70 prompts second LLM 80 (which may actually be the same as first LLM 74) with a second subquery (e.g., second prompt 78) requesting a label 50, 122 that answers the respective specification 45 of the input query based on the set of zero or more quotes that that was output for that query specification 45 applied to that clinical note 47, yielding an output response 82 for each paired query specification 45 and clinical note 47. For example, with reference to FIG. 2A, the second prompt 72 may ask "Do the snippets, when analyzed together, imply or strongly suggest that the patient has severe dementia? Answer (A) Patient has severe dementia, (B) Evidence suggests possible severe dementia, (C) Evidence against severe dementia, (D) Inconclusive evidence, or (E) No evidence or insufficient evidence. Include quotes to justify the answer." In response, for clinical note ABCDE1, the output response 80 includes label 122(*a*) "yes" and the most relevant quotes 124, including "Patient has an MMSE score of 7" 124(*a*)(1) and "Mental Status: Incoherent" 124(*a*)(2).

In sub-step 236, LLM system 70 prompts first LLM 74 with an advanced query (e.g., first prompt 72) that simultaneously asks the LLM 74 to (a) generate a set of zero or more quotes 124 from each clinical note 47 of the training set 46 that potentially supports the respective specification 45 of a query and (b) generate a label 50, 122 that answers the respective specification 45 of that query based on the set of zero or more quotes from each clinical note 47 that potentially supports the respective specification 45 of that query. For example, with reference to FIG. 2A, the first prompt 72 may ask "Does the input clinical note imply or strongly suggest that the patient has severe dementia with an MMSE less than 10? Answer (A) Patient has severe dementia, (B) Evidence suggests possible severe dementia, (C) Evidence against severe dementia, (D) Inconclusive evidence, or (E) No evidence or insufficient evidence. Include quotes to justify the answer." In response, for clinical note ABCDF15, the output response 80 includes label 122(*c*) "explicit no" and the most relevant quote(s) 124, including "Mental Status: Clear and coherent" 124(*c*)(1).

The output response 82 for each paired query specification 45(X) and training clinical note 47(Y) becomes the respective response 49(X)(Y) of the training response set 48.

In some embodiments, in step 240, note query application 42 performs a clustering operation on the responses 49 for a subset of the training set 46 of clinical notes 47, the clustering operation dividing those responses 49 into a plurality of clusters of responses, each respective cluster being supported by a respective class of evidence. It should be understood that the clusters may include overlapping responses 49, if, for example, certain responses 49 have quotes 124 that support several different classes of evidence. The clustering operation may be performed by an LLM, a neural network, some other form of artificial intelligence, or a combination thereof. The clustering operation may include unsupervised learning. The clustering operation will be explained in more detail below in connection with FIG. 4.

In step 250, for at least one query of the first set, note query application 42 displays, to the user 41 (e.g., in UI 43), the label 50, 122 and evidence 52, 124 for each training clinical note 47 that was generated in response to the at least one query. For example, for a binary query, the set 114 of binary query responses 116 is displayed within a binary query validation window 110, as depicted in FIG. 2A. As another example, for a threshold query, the set 144 of threshold query responses 146 is displayed within a threshold query validation window 140, as depicted in FIG. 2B. As another example, for a multiple-choice query, the set 174 of binary query responses 176 is displayed within a multiple-choice query validation window 170, as depicted in FIG. 2C.

Figure 4:
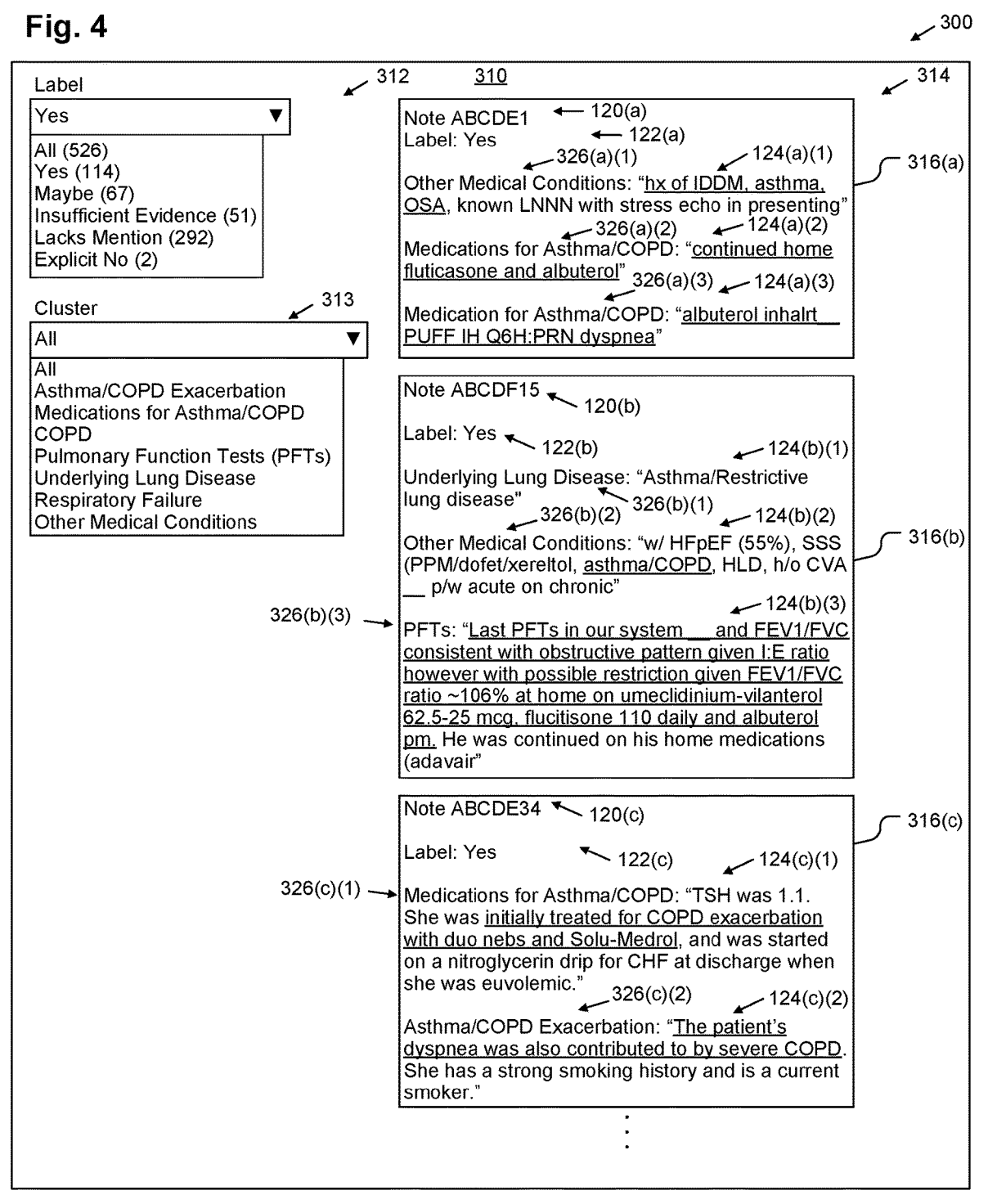

In some embodiments, step 250 may include sub-step 255, in which displaying the label 50, 122 and evidence 52, 124 for each training clinical note 47 is done on a cluster-by-cluster basis. Thus, as another example, after clustering step 240 is performed, in clustered configuration 300, a set 314 of clustered query responses 316 is displayed within a clustered validation window 310, as depicted in FIG. 4. Clustered validation window 310 also includes a first dropdown box 312 that allows the user 41 to select from a variety of labels 122 to use to filter the set 314 of clustered query responses 316 as well as a second dropdown box 313 that allows the user 41 to select from a variety of cluster labels 326 to use to further filter the set 314 of clustered query responses 316. Each clustered query responses 316 includes a note identifier 120, a label 122, and one or more pieces of evidence 124 (e.g., snippets or quotes from the clinical note 47 identified by the note identifier 120), with each piece of evidence 124 also including at least one cluster label 326 that describes that piece of evidence 124. It should be understood that the clinical labels themselves are generated by the LLM, neural network, or other form of artificial intelligence that performed the clustering operation based on the contents of the notes 47.

As depicted in FIG. 4, this example clustered validation window 310 was generated in response to a binary query asking whether or not the training clinical notes 47 support their respective patients having COPD or asthma, and dropdown box 312 shows a selection of "all," meaning that clustered query responses 316 having any label 122 are shown in set 314. As depicted, each label 122 in the dropdown box 312 includes the number of responses 314 that include that label 122. Thus, there are 526 total responses 316 when the set 314 is unfiltered, 114 responses 316 when the set 314 is filtered to only include "yes" labels, 67 responses 316 when the set 314 is filtered to only include "maybe" labels, 51 responses 316 when the set 314 is filtered to only include "insufficient evidence" labels, 292 responses 316 when the set 314 is filtered to only include "lacks mention" labels, and 2 responses 316 when the set 314 is filtered to only include "explicit no" labels. In some embodiments (not depicted), there may be one or more additional dropdown boxes that allow the user 41 to filter the set 314 using other criteria, such as, for example, note metadata (e.g., medical provider name, department, etc.).

As further depicted, dropdown box 313 shows a selection of "all," meaning that clustered query responses 316 having any cluster labels 326 are shown in set 314. The cluster labels 326 were generated by the clustering operation of step 240. Thus the clustering operation was able to predict which label(s) 122 to apply to each response 49(Q)(Y) to query 45(Q) on the basis of whether or not any of six classes of evidence ("Asthma/COPD Exacerbation," "Medications for Asthma/COPD," "COPD," "Pulmonary Function Tests (PFTs)," "Underlying Lung Disease," "Respiratory Failure," and "Other Medical Conditions") were present in any of the snippets 124. In some cases, certain snippets 124 did not fall into any of these classes, thereby being labeled "Other Medical Conditions."

As further depicted, clustered query response 316(*a*), which represents a training clinical note 47 with identifier 120(*a*) "ABCDE1," has label 122(*a*), indicating that the training label 50 assigned in response to the binary query for clinical note ABCDE1 is "yes," meaning that the patient has been positively identified as having Asthma or COPD. This evaluation is supported by three pieces of evidence: 124(*a*)(1) "hx of IDDM, asthma, OSA, known LNNN with stress echo in presenting," 124(*a*)(2) "continued home fluticasone and albuterol," and 124(*a*)(3) "albuterol inhalrt_PUFF IH Q6H:PRN dyspnea." Each piece of evidence 124 has a respective cluster label 326 identifying which class of evidence it is. Thus, as depicted, snippet 124(*a*)(1) has a cluster label 326(*a*)(1) identifying it as belonging to the "Other Medical Conditions" cluster, snippet 124(*a*)(2) has a cluster label 326(*a*)(2) identifying it as belonging to the "Medications for Asthma/COPD" cluster, and snippet 124(*a*)(3) has a cluster label 326(*a*)(3) identifying it as belonging to the "Medications for Asthma/COPD" cluster.

Similarly, clustered query response 316(*b*), which represents a training clinical note 47 with identifier 120(*b*) "ABCDF15," has label 122(*b*), indicating that the training label 50 assigned in response to the binary query for clinical note ABCDF15 is "yes," meaning that the patient has been positively identified as having Asthma or COPD. This evaluation is supported by three pieces of evidence: 124(*b*)(1) "Asthma/Restrictive lung disease," 124(*b*)(2) "w/HFpEF (55%), SSS (PPM/dofet/xereltol, asthma/COPD, HLD, h/o CVA_p/w acute on chronic," and 124(*b*)(3) "Last PFTs in our system and FEV1/FVC consistent with obstructive pattern given I:E ratio however with possible restriction given FEV1/FVC ratio ~106% at home on umeclidinium-vilanterol 62.5-25 mcg, flucitisone 110 daily and albuterol pm. He was continued on his home medications (adavair." Each piece of evidence 124 has a respective cluster label 326 identifying which class of evidence it is. Thus, as depicted, snippet 124(*b*)(1) has a cluster label 326(*b*)(1) identifying it as belonging to the "Underlying Lung Disease" cluster, snippet 124(*b*)(2) has a cluster label 326(*b*)(2) identifying it as belonging to the "Other Medical Conditions" cluster, and snippet 124(*b*)(3) has a cluster label 326(*b*)(3) identifying it as belonging to the "PFTs" cluster.

Similarly, clustered query response 316(*c*), which represents a training clinical note 47 with identifier 120(*c*) "ABCDE34," has label 122(*c*), indicating that the training label 50 assigned in response to the binary query for clinical note ABCDE34 is "yes," meaning that the patient has been positively identified as having Asthma or COPD. This evaluation is supported by two pieces of evidence: 124(*c*)(1) "Asthma/Restrictive lung disease" and 124(*c*)(2) "w/HFpEF (55%), SSS (PPM/dofet/xereltol, asthma/COPD, HLD, h/o CVA_p/w acute on chronic." Each piece of evidence 124 has a respective cluster label 326 identifying which class of evidence it is. Thus, as depicted, snippet 124(*c*)(1) has a cluster label 326(*c*)(1) identifying it as belonging to the "Medications for Asthma/COPD" cluster and snippet 124(*c*)(2) has a cluster label 326(*c*)(2) identifying it as belonging to the "Asthma/COPD Exacerbation" cluster.

In some embodiments, as depicted, part of all or some of the snippets 124 is underlined (or otherwise highlighted), indicating which specific part of that snippet 124 supports the cluster classification. In some embodiments (not depicted), a snippet 124 that contains support for two different clusters may include color-coded highlighting that identifies what part of that snippet 124 supports each cluster classification.

Returning to FIG. 3, in step 260, in response to displaying in step 250, note query application 42 receives a revised query specification 55 for the at least one query whose results were displayed in step 250. As with step 210, in some embodiments, step 260 may include displaying a binary query input window 102, a threshold query input window 132, or a multiple-choice query input window 162 in UI 43 for the at least one query to allow the user 41 to input a revised binary query specification, threshold query specification, or multiple-choice query specification as described in connection with FIGS. 2A, 2B, and 2C. In some embodiments, user 41 may also input a revised query specification 55 by uploading a revised dictionary definition file (not depicted) that defines the a term used in the revised query specification 55 in detail. For example, after displaying the threshold query validation window 140 from FIG. 2B, the user 41 may decide that the threshold value of 1.04 was not a helpful value, so the user 41 may select the creatinine threshold query for revision, causing the note query application 42 to re-display threshold query input window 132 in UI 43, this time with the values of elements 134, 136, 138 pre-populated with the previously-entered values (i.e., ">," "Creatinine," and "1.04"). Then the user 41 may use input device 38 to update the value in the value text box 138 to be 1.05, for example.

In some cases, step 260 may include sub-step 262 or 264. In sub-step 262, the revised query specification 55 excludes clinical notes 47 that are primarily supported by a particular class of evidence associated with a particular cluster label 326. For example, in the case of FIG. 4, the user 41 may realize that underlying lung disease is sufficiently different from all the other cluster labels 326, so user 41 may decide to exclude underlying lung disease from the definition within definition text box 108. Thus, clusters can easily be used to carve out pieces of evidence for a given category. As another example, suppose while analyzing clusters for a generic "diabetes" task, the user 41 sees that there is a cluster of evidence for the "yes" results that relate to "gestational diabetes," which is an often temporary form of diabetes that women experience during pregnancy. The user 41 may then realize they "gestational diabetes" should not be counted in the definition of diabetes for the particular use case. The user 41 could rectify this by "carving out" gestational diabetes from the task definition by modifying the definition within definition text box 108 (or within a revised dictionary definition file) to explicitly exclude gestational diabetes.

In sub-step 264, the revised query specification 55 adds clinical notes 47 that are primarily supported by a particular class of evidence associated with a particular cluster label 326. Thus, clusters can also be used to "carve in" pieces of evidence that the user 41 intended to include in their definition. For example, suppose a user 41 is interested in determining whether patients were administered anti-sepsis treatments, and initially defines anti-sepsis treatments as "antibiotics, steroids, or intubation." However, when analyzing clusters of evidence for the "insufficient evidence" label 122, the user 41 notices that there is a cluster of results that mention BiPaP/CPAP machines as insufficient evidence for antisepsis treatments. The user 41 quickly realizes that he or she meant to include mechanical ventilation techniques like BiPaP/CPAP as an anti-sepsis treatment, but didn't recognize this when initially creating the treatment definition because it was closely related to (yet subtly different from) intubation. The user 41 can now go back and edit the original definition to include mechanical ventilation techniques by modifying the definition within definition text box 108 (or within a revised dictionary definition file).

In step 270, updates the query specification 45(X) corresponding to the revised query specification 55 to reflect the revised query specification 55, and then operation proceeds back to step 230, so that the LLM system 70 can evaluate at least the affected query specification 45(X) again, as revised.

Figure 5:
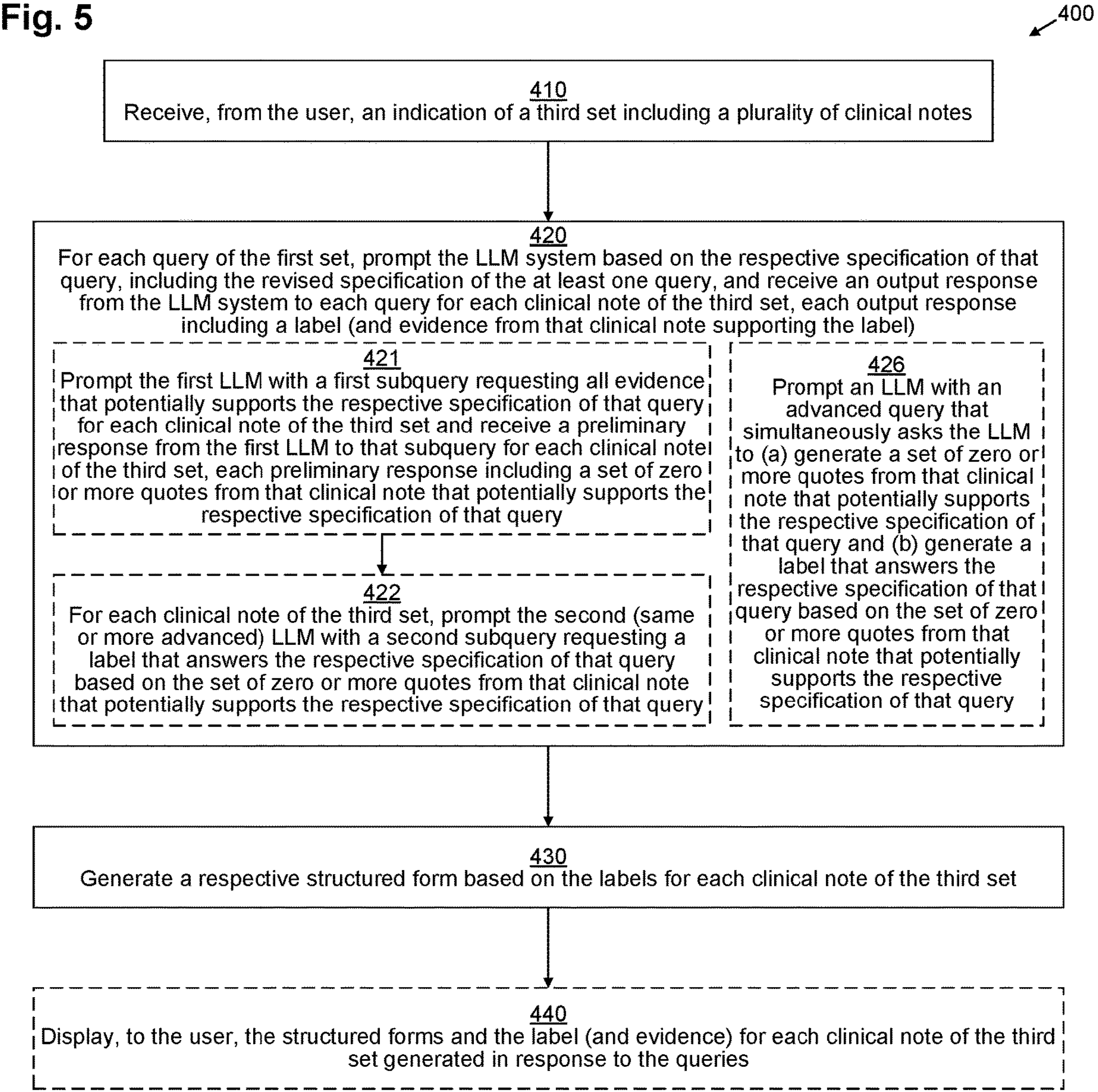
FIG. 5 illustrates an example method in accordance with one or more embodiments.

FIG. 5 illustrates an example method 400 performed by a system 30 for performing an analysis using the set 44 of query specifications 45. Method 400 is typically performed once method 200 has already completed.

In step 410, note query application 42 receives, from the user 41, an indication of a production set 56 of clinical notes 57. Step 410 may include user 41 selecting a location where the production set 56 is stored, the user 41 scanning in or copying the production set 56 into memory 40, the user 41 typing in the clinical notes 57 of production set 56, or some combination of these (e.g., some clinical notes 57 are scanned, some are uploaded, and some are typed in by the user 41).

In step 420, for each query of the first set, note query application 42 prompts LLM system 70 based on the respective specification 45 of that query (with first prompt 72) and receives a response 59, 82 from the LLM system 70 to each query for each clinical note 57 of the production set 56, each response 59, 82 including a label 60 and, in some embodiments, evidence 62 from that clinical note 57 supporting the label 60. Thus, for all N production notes 57, there are P responses 49(1-P)(1-N), and production response set 58 has P×N responses 59.

In some embodiments, step 420 may include sub-steps 421, 422 for each query of the first set, while in other embodiments, step 420 includes sub-step 426 for each query of the first set. Sub-steps 421, 422 correspond to sub-steps 231, 232, respectively, from method 200 but are performed on the production set 56 of notes 57 instead of the training set 46 of notes 47. Similarly, sub-step 426 corresponds to sub-step 236 from method 200 but is performed on the production set 56 of notes 57 instead of the training set 46 of notes 47. In some embodiments, sub-steps 422 and 426 do output evidence 62 for each output response 82 (unless the label is "lacks mention"), while in other embodiments, sub-steps 422 and 426 do not output evidence 62 for the output responses 82.

In step 430, note query application 42 generates a respective structured form 64 based on the labels 59 for each clinical note of the production set 56. Thus, for production note 57(1), step 430 generates structured form 65(1), which is based on the labels 60 (1-P)(1); for production note 57(2), step 430 generates structured form 65(2), which is based on the labels 60 (1-P)(2); etc.

In some embodiments, in step 440, note query application 42 displays the structured forms 65 and/or the labels 60 (with the evidence 62, in some embodiments) to the user 41 in UI 43.

Figure 6:
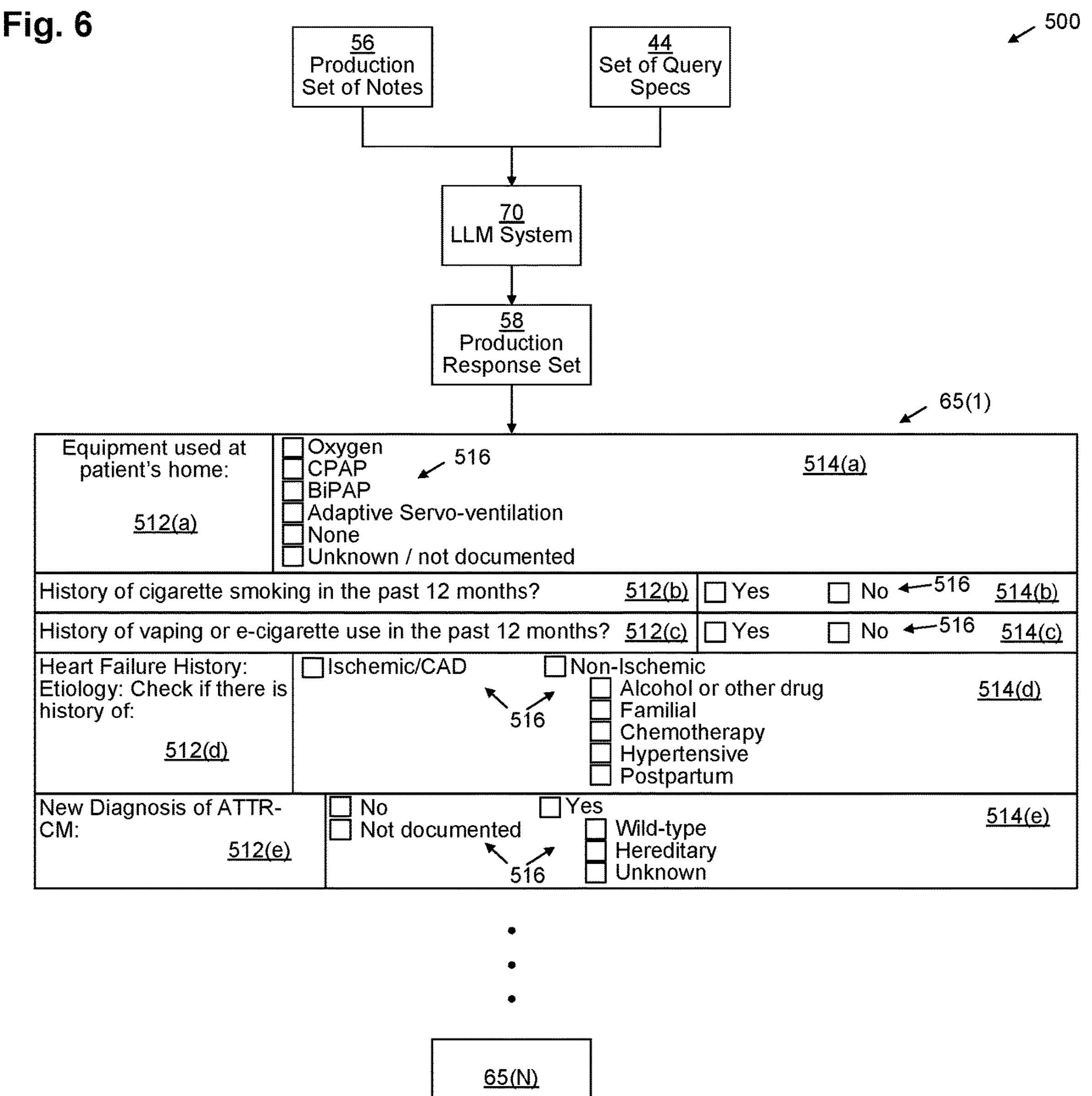
FIG. 6 illustrates an example arrangement of data structures in accordance with one or more embodiments.

FIG. 6 depicts an example arrangement 500 of data structures used in conjunction with method 400. Production set 56 of clinical notes 57 and set 44 of query specifications 45 are input into LLM system 70, which outputs production set 58 of responses 59, which are used to generate the set of structured forms 65 (1-N). Each structured form 65 includes field descriptors 512 and accompanying field value areas 514, each of which includes at least one field value elements 516. In step 430, note query application 42 selects a particular field value element (or elements) 516 in each field area 514 based on the responses 59 for a particular production note 59.

Thus, for example, as depicted in FIG. 6, field descriptor 512(*a*) is entitled "Equipment used at patient's home," and accompanying field value area 514(*a*) includes field value elements 516 entitled "Oxygen," "CPAP," "BiPAP," "Adaptive Servo-ventilation," "None," and "Unknown/not documented," representing different possible values that the equipment used at home can take. Field descriptor 512(*b*) is entitled "History of cigarette smoking in the past 12 months?", and accompanying field value area 514(*b*) includes field value elements 516 entitled "Yes" and "No." Field descriptor 512(*c*) is entitled "History of vaping or e-cigarette use in the past 12 months?", and accompanying field value area 514(*c*) includes field value elements 516 entitled "Yes" and "No."

Field descriptor 512(*d*) is entitled "Heart Failure History:" with instructions "Etiology: Check if there is history of:", and accompanying field value area 514(*d*) includes field value elements 516 entitled "ischemic/CAD," "non-ischemic: alcohol or other drug," "non-ischemic: familial," "non-ischemic: chemotherapy," "non-ischemic: hypertensive," and "non-ischemic: postpartum," representing the different possible values that the etiology of heart failure history can take. In an example embodiment, field value area 514(*d*) may be filled out based on the responses 59 generated in response to the query defined by the query specification 45 defined in FIG. 2B.

Additional field descriptors 512 (e.g., 512(*e*)) and corresponding field value areas 514 (e.g., 514(*e*)) may also be depicted on forms 65 as well.

While various embodiments of the invention have been particularly shown and described, it will be understood by those skilled in the art that various changes in form and details may be made therein without departing from the spirit and scope of the invention as defined by the appended claims.

It should be understood that although various embodiments have been described as being methods, software embodying these methods is also included. Thus, one embodiment includes at least one tangible computer-readable medium (such as, for example, a hard disk, a floppy disk, an optical disk, computer memory, flash memory, etc.) programmed with instructions, which, when performed by a computer or a set of computers, cause one or more of the methods described in various embodiments to be performed. Another embodiment includes a computer which is programmed to perform one or more of the methods described in various embodiments.

Furthermore, it should be understood that all embodiments which have been described may be combined in all possible combinations with each other, except to the extent that such combinations have been explicitly excluded.

Finally, nothing in this Specification shall be construed as an admission of any sort. Even if a technique, method, apparatus, or other concept is specifically labeled as "background" or as "conventional," Applicants make no admission that such technique, method, apparatus, or other concept is actually prior art under 35 U.S.C. § 102 or 103, such determination being a legal determination that depends upon many factors, not all of which are known to Applicants at this time.

What is claimed is:

1. A method performed by a computing system, the method comprising:

for each of a first set of one or more queries, receiving, from a user, a respective specification of that query;

receiving, from the user, an indication of a second set including a plurality of clinical notes;

for each query of the first set, prompting a large language model (LLM) system based on the respective specification of that query and receiving a response from the LLM system to each query for each clinical note of the second set, each response including a label and evidence from that clinical note supporting the label;

for at least one query of the first set, displaying, to the user, the label and evidence for each clinical note of the second set generated in response to the at least one query;

in response to displaying, receiving, from the user, a revised specification of the at least one query; and prompting the LLM system based on the revised specification of the at least one query and receiving an updated response from the LLM system to the at least one query for each clinical note of the second set, each updated response including an updated label and updated evidence from that clinical note supporting the updated label.

2. The method of claim 1 wherein prompting the LLM system based on the respective specification of that query includes:

prompting a first LLM with a first subquery requesting all evidence that potentially supports the respective specification of that query for each clinical note of the second set and receiving a preliminary response from the first LLM to that subquery for each clinical note of the second set, each preliminary response including a set of zero or more quotes from that clinical note that potentially supports the respective specification of that query; and for each clinical note of the second set, prompting a second LLM with a second subquery requesting a label that answers the respective specification of that query based on the set of zero or more quotes from that clinical note that potentially supports the respective specification of that query.

3. The method claim 2 wherein the first LLM is the same as the second LLM.

4. The method of claim 2 wherein the second LLM is more advanced than the first LLM.

5. The method of claim 1 wherein prompting the LLM system based on the respective specification of that query includes: prompting an LLM with an advanced query that simultaneously asks the LLM to (a) generate a set of zero or more quotes from that clinical note that potentially supports the respective specification of that query and (b) generate a label that answers the respective specification of that query based on the set of zero or more quotes from that clinical note that potentially supports the respective specification of that query.

6. The method of claim 1 wherein:

the method further comprises performing a clustering operation on the responses for a subset of the clinical notes, the clustering operation dividing those responses into a plurality of clusters of responses, each respective cluster being supported by a respective class of evidence; and displaying the label and evidence for each clinical note of the second set includes displaying the label and evidence for each clinical note of the second set on a cluster-by-cluster basis.

7. The method of claim 6 wherein the revised specification of the at least one query excludes responses that are supported by a particular class of evidence associated with a particular cluster of the plurality of clusters.

8. The method of claim 6 wherein the revised specification of the at least one query adds responses that are supported by a particular class of evidence associated with a particular cluster of the plurality of clusters.

9. The method of claim 1 wherein the method further comprises:

receiving, from the user, an indication of a third set of a plurality of clinical notes;

for each query of the first set, prompting the LLM system based on the respective specification of that query, including the revised specification of the at least one query, and receiving an output response from the LLM system to each query for each clinical note of the third set, each output response including a label; and in response to receiving the output response from the LLM system to each query for each clinical note of the third set, generating a respective structured form based on the labels for each clinical note of the third set.

10. The method of claim 9 wherein:

each output response includes evidence from its respective clinical note supporting the label for that output response; and the method further comprises displaying evidence from a clinical note of the third set supporting the label for its output response.

11. The method of claim 1 wherein:

receiving the specification of a first query from the user includes receiving a natural language description of one of a medical condition, medication, treatment, status, and procedure; and labels in response to the first query include labels indicating: yes, maybe, insufficient evidence, lacks mention, and explicit no.

12. The method of claim 1 wherein:

receiving the specification of a first query from the user includes receiving a description of a value type, a threshold value, and a comparator; and labels in response to the first query include labels indicating: yes, insufficient evidence, lacks mention, and explicit no.

13. The method of claim 1 wherein receiving the specification of a first query from the user includes receiving:

a natural language description of a category including one of a medical condition, medication, treatment, status, and procedure; and labels indicating possible values of the category.

14. A computer program product comprising a non-transitory computer-readable storage medium storing instructions, which, when performed by processing circuitry of a computing system, causes the computing system to perform the following operations:

for each of a first set of one or more queries, receiving, from a user, a respective specification of that query;

receiving, from the user, an indication of a second set including a plurality of clinical notes;

for each query of the first set, prompting a large language model (LLM) system based on the respective specification of that query and receiving a response from the LLM system to that query for each clinical note of the second set, each response including a label and evidence from that clinical note supporting the label;

for at least one query of the first set, displaying, to the user, the label and evidence for each clinical note of the second set generated in response to the at least one query;

in response to displaying, receiving, from the user, a revised specification of the at least one query; and prompting the LLM system based on the revised specification of the at least one query and receiving an updated response from the LLM system to the at least one query for each clinical note of the second set, each updated response including an updated label and updated evidence from that clinical note supporting the updated label.

15. The computer program product of claim 14 wherein prompting the LLM system based on the respective specification of that query includes:

prompting a first LLM with a first subquery requesting all evidence that potentially supports the respective specification of that query for each clinical note of the second set and receiving a preliminary response from the first LLM to that subquery for each clinical note of the second set, each preliminary response including a set of zero or more quotes from that clinical note that potentially supports the respective specification of that query; and for each clinical note of the second set, prompting a second LLM with a second subquery requesting a label that answers the respective specification of that query based on the set of zero or more quotes from that clinical note that potentially supports the respective specification of that query.

16. The computer program product of claim 14 wherein prompting the LLM system based on the respective specification of that query includes: prompting an LLM with an advanced query that simultaneously asks the LLM to (a) generate a set of zero or more quotes from that clinical note that potentially supports the respective specification of that query and (b) generate a label that answers the respective specification of that query based on the set of zero or more quotes from that clinical note that potentially supports the respective specification of that query.

17. The computer program product of claim 14 wherein:

the instructions, when performed by the processing circuitry, further cause the computing system to perform a clustering operation on the responses for a subset of the clinical notes, the clustering operation dividing those responses into a plurality of clusters of responses, each respective cluster being supported by a respective class of evidence; and displaying the label and evidence for each clinical note of the second set includes displaying the label and evidence for each clinical note of the second set on a cluster-by-cluster basis.

18. The computer program product of claim 14 wherein the instructions, when performed by the processing circuitry, further cause the computing system to perform the following operations:

receiving, from the user, an indication of a third set of a plurality of clinical notes;

for each query of the first set, prompting the LLM system based on the respective specification of that query, including the revised specification of the at least one query, and receiving an output response from the LLM system to each query for each clinical note of the third set, each output response including a label; and in response to receiving the output response from the LLM system to each query for each clinical note of the third set, generating a respective structured form based on the labels for each clinical note of the third set.

19. The computer program product of claim 14 wherein:

receiving the specification of a first query from the user includes receiving a natural language description of one of a medical condition, medication, treatment, status, and procedure; and labels in response to the first query include labels indicating: yes, maybe, insufficient evidence, lacks mention, and explicit no.

20. A computing system comprising:

interface circuitry; and processing circuitry coupled to memory configured to:

for each of a first set of one or more queries, receive, from a user via the interface circuitry, a respective specification of that query;

receive, from the user via the interface circuitry, an indication of a second set including a plurality of clinical notes;

for each query of the first set, prompt a large language model (LLM) system based on the respective specification of that query and receive a response from the LLM system to that query for each clinical note of the second set, each response including a label and evidence from that clinical note supporting the label;

for at least one query of the first set, display, to the user via the interface circuitry, the label and evidence for each clinical note of the second set generated in response to the at least one query;

in response to displaying, receive, from the user via the interface circuitry, a revised specification of the at least one query; and prompt the LLM system based on the revised specification of the at least one query and receive an updated response from the LLM system to the at least one query for each clinical note of the second set, each updated response including an updated label and updated evidence from that clinical note supporting the updated label.

* * * * *